US006425856B1

(12) United States Patent
Shapland et al.

(10) Patent No.: US 6,425,856 B1
(45) Date of Patent: Jul. 30, 2002

(54) CARDIAC DISEASE TREATMENT AND DEVICE

(75) Inventors: J. Edward Shapland, Vadnais Heights; Robert G. Walsh, Lakeville; John David Dockter, Brooklyn Park, all of MN (US)

(73) Assignee: Acorn Cardiovascular, Inc., St. Paul, MN (US)

(*) Notice: Subject to any disclaimer, the term of this patent is extended or adjusted under 35 U.S.C. 154(b) by 0 days.

(21) Appl. No.: 09/567,726

(22) Filed: May 10, 2000

(51) Int. Cl.[7] ................................................ A61F 13/00
(52) U.S. Cl. .......................................... 600/37; 600/16
(58) Field of Search ............................. 600/16–18, 37; 128/898; 606/157; 623/66.1

(56) References Cited

U.S. PATENT DOCUMENTS

| 3,983,863 A | 10/1976 | Janke et al. |
| 4,048,990 A | 9/1977 | Goetz |
| 4,428,375 A | 1/1984 | Ellman |
| 4,630,597 A | 12/1986 | Kantrowitz et al. |
| 4,690,134 A | 9/1987 | Snyders |

(List continued on next page.)

FOREIGN PATENT DOCUMENTS

| DE | 295 17 393 U 1 | 3/1996 |
| EP | 0 280 564 A2 | 8/1988 |
| JP | 60-203250 A2 | 10/1985 |
| JP | 01-145066 A | 6/1989 |
| SU | 1009457 A | 4/1983 |
| WO | WO 98/29041 | 7/1998 |
| WO | WO 98/58598 | 12/1998 |
| WO | WO 99/44534 | 9/1999 |
| WO | WO 00/06026 | 2/2000 |
| WO | WO 00/06027 | 2/2000 |
| WO | WO 00/06028 | 2/2000 |
| WO | WO 00/16700 | 3/2000 |
| WO | WO 01/02500 A1 | 1/2001 |

OTHER PUBLICATIONS

Levin, H. et al., "Reversal of Chronic Ventricular Dilation in Patients With End–Stage Cardiomyopathy by Prolonged Mechanical Unloading", *Circulation*, vol. 91, No. 11, pp. 2717–2720 (Jun. 1, 1995).

(List continued on next page.)

*Primary Examiner*—John P. Lacyk
*Assistant Examiner*—Joseph A. Cadugan
(74) *Attorney, Agent, or Firm*—Merchant & Gould P.C.

(57) ABSTRACT

A cardiac constraint device comprising a jacket of biological compatible material and an adjustment member. The jacket is adapted to be secured to the heart to snugly conform to an external geometry of the heart and assume a maximum adjusted volume to constrain circumferential expansion of the heart beyond the maximum adjusted volume during diastole and to permit unimpeded contraction of the heart during systole. The adjustment mechanism is configured to alter the internal volume defined by the jacket after the jacket is secured to the heart. The invention also provides a method for treating cardiac disease.

5 Claims, 11 Drawing Sheets

U.S. PATENT DOCUMENTS

| | | | |
|---|---|---|---|
| 4,821,723 A | | 4/1989 | Baker, Jr. et al. |
| 4,840,626 A | * | 6/1989 | Linsky et al. ............. 600/37 X |
| 4,878,890 A | | 11/1989 | Bilweis |
| 4,936,857 A | | 6/1990 | Kulik |
| 4,957,477 A | | 9/1990 | Lundbäck |
| 4,973,300 A | | 11/1990 | Wright |
| 4,976,730 A | | 12/1990 | Kwan-Gett |
| 5,057,117 A | | 10/1991 | Atweh |
| 5,087,243 A | | 2/1992 | Avitall |
| 5,131,905 A | | 7/1992 | Grooters |
| 5,150,706 A | | 9/1992 | Cox et al. |
| 5,186,711 A | | 2/1993 | Epstein |
| 5,192,314 A | | 3/1993 | Daskalakis |
| 5,256,132 A | | 10/1993 | Snyders |
| 5,279,539 A | * | 1/1994 | Bohan et al. .................. 600/37 |
| 5,290,217 A | | 3/1994 | Campos |
| 5,356,432 A | | 10/1994 | Rutkow et al. |
| 5,383,840 A | | 1/1995 | Heilman et al. |
| 5,385,156 A | | 1/1995 | Oliva |
| 5,429,584 A | | 7/1995 | Chiu |
| 5,507,779 A | | 4/1996 | Altman |
| 5,524,633 A | | 6/1996 | Heaven et al. |
| 5,593,441 A | * | 1/1997 | Lichtenstein et al. ..... 600/37 X |
| 5,603,337 A | | 2/1997 | Jarvik |
| 5,647,380 A | | 7/1997 | Campbell et al. |
| 5,695,525 A | * | 12/1997 | Mulhauser et al. ....... 600/37 X |
| 5,702,343 A | | 12/1997 | Alferness |
| 5,713,954 A | | 2/1998 | Rosenberg et al. |
| 5,782,746 A | * | 7/1998 | Wright ........................ 600/37 |
| 5,800,528 A | | 9/1998 | Lederman et al. |
| 5,853,422 A | * | 12/1998 | Huebsch et al. ............ 606/213 |
| 5,961,440 A | | 10/1999 | Schweich, Jr. et al. |
| 5,990,378 A | | 11/1999 | Ellis |
| 6,045,497 A | | 4/2000 | Schweich, Jr. et al. |
| 6,050,936 A | | 4/2000 | Schweich, Jr. et al. |
| 6,059,715 A | | 5/2000 | Schweich, Jr. et al. |
| 6,077,214 A | * | 6/2000 | Mortier et al. ................ 600/16 |
| 6,085,754 A | * | 7/2000 | Alferness et al. ......... 600/37 X |
| 6,095,968 A | * | 8/2000 | Snyders ........................ 600/16 |
| 6,155,972 A | * | 12/2000 | Nauertz et al. ................ 600/37 |
| 6,193,648 B1 | * | 2/2001 | Krueger ........................ 600/37 |
| 6,230,714 B1 | * | 5/2001 | Alferness et al. ......... 600/37 X |
| 6,241,654 B1 | * | 6/2001 | Alferness ..................... 600/37 |

OTHER PUBLICATIONS

Oh, J. et al., "The Effects Of Prosthetic Cardiac Binding and Adynamic Cardiomyoplasty In A Model Of Dilated Cardiomyopathy", *The Journal of Thoracic and Cardiovascular Surgery*, vol. 116, No. 1, pp. 148–153 (Jul. 1998).

Paling, D., "Warp Knitting Technology", *Columbine Press*, p. 111 (1965).

Vaynblat, M. et al., "Cardiac Binding in Experimental Heart Failure", *Ann. Thorac. Surg.*, vol. 64, 11 pages, (1997).

"Supplement to Circulation", *Abstracts from the 68th Scientific Sessions*, vol. 92, No. 8, 2 pages (Oct. 15, 1995).

Capomolla, S. et al., "Dobutamine and nitroprusside infusion in patients with severe congestive heart failure: Hemodynamic improvement by discordant effects on mitral regurgitation, left atrial function, and ventricular function", *American Heart Journal*, pp. 1089–1098 (Dec. 1997).

Capouya, E. et al., "Girdling Effect of Nonstimulated Cardiomyoplasty on Left Ventricular Function", *Ann Thorac. Surg.*, vol. 56, pp. 867–871 (1993).

Cohn, J., "The Management of Chronic Heart Failure", *The New England Journal of Medicine*, vol. 335, No. 7, pp. 490–498 (Aug. 15, 1996).

Coletta, C. et al., Prognostic value of left ventricular volume response during dobutamine stress echocardiography:, *European Heart Journal*, vol. 18, pp. 1599–1605 (Oct. 1997).

Guasp, F., "Una prótesis contentiva para el tratamiento de la miocardiopatía dilatada", *Revista Española de Cardiología*, vol. 51, No. 7, pp. 521–528 (Jul. 1998).

Kass, D. et al., "Reverse Remodeling From Cardiomyoplasty in Human Heart Failure External Constraint Versus Active Assist", *Circulation*, vol. 91, No. 9, pp. 2314–2318 (May 1, 1995).

* cited by examiner

CARDIAC DISEASE TREATMENT AND DEVICE

FIELD OF THE INVENTION

The present invention pertains to a device and method for treating congestive heart disease and related valvular dysfunction. More particularly, the present invention is directed to a cardiac constraint that is adjustable after implantation.

BACKGROUND OF THE INVENTION

Congestive heart disease is a progressive and debilitating illness. The disease is characterized by a progressive enlargement of the heart. As the heart enlarges, the heart is performing an increasing amount of work in order to pump blood each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Patients suffering from congestive heart disease are commonly grouped into four classes (i.e., Classes I, II, III and IV). In the early stages (e.g., Classes I and II), drug therapy is the commonly proscribed treatment. Drug therapy treats the symptoms of the disease and may slow the progression of the disease. Importantly, there is no cure for congestive heart disease. Even with drug therapy, the disease will progress. Further, the drugs may have adverse side effects.

Presently, the only permanent treatment for congestive heart disease is heart transplant. To qualify, a patient must be in the later stage of the disease (e.g., Classes III and IV with Class IV patients given priority for transplant). Such patients are extremely sick individuals. Class III patients have marked physical activity limitations and Class IV patients are symptomatic even at rest.

Due to the absence of effective intermediate treatment between drug therapy and heart transplant, Class III and IV patients will have suffered terribly before qualifying for heart transplant. Further, after such suffering, the available treatment is unsatisfactory. Heart transplant procedures are very risky, extremely invasive and expensive and only shortly extend a patient's life. For example, prior to transplant, a Class IV patient may have a life expectancy of 6 months to one-year. Heart transplant may improve the expectancy to about five years.

Unfortunately, not enough hearts are available for transplant to meet the needs of congestive heart disease patients. In the United States, in excess of 35,000 transplant candidates compete for only about 2,000 transplants per year. A transplant waiting list is about 8–12 months long on average and frequently a patient may have to wait about 1–2 years for a donor heart. While the availability of donor hearts has historically increased, the rate of increase is slowing dramatically. Even if the risks and expense of heart transplant could be tolerated, this treatment option is becoming increasingly unavailable. Further, many patient's do not qualify for heart transplant for failure to meet any one of a number of qualifying criteria.

Congestive heart failure has an enormous societal impact. In the United States alone, about five million people suffer from the disease (Classes I through IV combined). Alarmingly, congestive heart failure is one of the most rapidly accelerating diseases. (about 400,000 new patients in the United States each year). Economic costs of the disease have been estimated at $38 billion annually.

Not surprising, substantial effort has been made to find alternative treatments for congestive heart disease. Recently, a new surgical procedure has been developed. Referred to as the Batista procedure, the surgical technique includes dissecting and removing portions of the heart in order to reduce heart volume. This is a radical new and experimental procedure subject to substantial controversy. Furthermore, the procedure is highly invasive, risky and expensive and commonly includes other expensive procedures (such as a concurrent heart valve replacement). Also, the treatment is limited to Class IV patients and, accordingly, provides no hope to patients facing ineffective drug treatment prior to Class IV. Finally, if the procedure fails, emergency heart transplant is the only available option.

Clearly, there is a need for alternative treatments applicable to both early and later stages of the disease to either stop the progressive nature of the disease or more drastically slow the progressive nature of congestive heart disease. Unfortunately, currently developed options are experimental, costly and problematic.

Cardiomyoplasty is a recently developed treatment for earlier stage congestive heart disease (e.g., as early as Class III dilated cardiomyopathy). In this procedure, the latissimus dorsi muscle (taken from the patient's shoulder) is wrapped around the heart and chronically paced synchronously with ventricular systole. Pacing of the muscle results in muscle contraction to assist the contraction of the heart during systole.

While cardiomyoplasty has resulted in symptomatic improvement, the nature of the improvement is not understood. For example, one study has suggested the benefits of cardiomyoplasty are derived less from active systolic assist than from remodeling, perhaps because of an external elastic constraint. The study suggests an elastic constraint (i.e., a non-stimulated muscle wrap or an artificial elastic sock placed around the heart) could provide similar benefits. Kass et al., Reverse Remodeling From Cardiomyoplasty In Human Heart Failure: External Constraint Versus Active Assist, 91 *Circulation* 2314–2318 (1995).

Even though cardiomyoplasty has demonstrated symptomatic improvement, studies suggest the procedure only minimally improves cardiac performance. The procedure is highly invasive requiring harvesting a patient's muscle and an open chest approach (i.e., sternotomy) to access the heart. Furthermore, the procedure is expensive—especially those using a paced muscle. Such procedures require costly pacemakers. The cardiomyoplasty procedure is complicated. For example, it is difficult to adequately wrap the muscle around the heart with a satisfactory fit. Also, if adequate blood flow is not maintained to the wrapped muscle, the muscle may necrose. The muscle may stretch after wrapping reducing its constraining benefits and is generally not susceptible to post-operative adjustment. Finally, the muscle may fibrose and adhere to the heart causing undesirable constraint on the contraction of the heart during systole. In addition to cardiomyoplasty, mechanical assist devices have been developed as intermediate procedures for treating congestive heart disease. Such devices include left ventricular assist devices ("LVAD") and total artificial hearts ("TAH"). An LVAD includes a mechanical pump for urging blood flow from the left ventricle and into the aorta. An example of such is shown in U.S. Pat. No. 4,995,857 to Arnold dated Feb. 26, 1991. TAH devices, such as the celebrated Jarvik heart, are used as temporary measures while a patient awaits a donor heart for transplant.

Other attempts at cardiac assist devices are found in U.S. Pat. No. 4,957,477 to Lundbäck dated Sep. 18, 1990, U.S. Pat. No. 5,131,905 to Grooters dated Jul. 21, 1992 and U.S. Pat. No. 5,256,132 to Snyders dated Oct. 26, 1993. Both of the Grooters and Snyders patents teach cardiac assist devices which pump fluid into chambers opposing the heart to assist systolic contractions of the heart. The Lundbäck patent teaches a double-walled jacket surrounding the heart. A fluid fills a chamber between the walls of the jacket. The inner wall is positioned against the heart and is pliable to move with the heart. Movement of the heart during beating displaces fluid within the jacket chamber.

Commonly assigned U.S. Pat. No. 5,702,343 to Alferness dated Dec. 30, 1997 (corresponding to PCT Application WO 98/14136, published Apr. 9, 1998) teaches a jacket to constrain cardiac expansion during diastole. The present invention pertains to improvements to the invention disclosed in the '343 patent.

SUMMARY OF THE INVENTION

According to a preferred embodiment of the present invention, a method and device are disclosed for treating congestive heart disease and related cardiac complications such as valvular disorders. The invention includes a jacket of biologically compatible material. The jacket has an internal volume dimensioned for an apex of the heart to be inserted into the volume and for the jacket to be slipped over the heart. The jacket has a longitudinal dimension between upper and lower ends sufficient for the jacket to surround a lower portion of the heart. Preferably, the jacket is configured to surround a valvular annulus of the heart and at least the ventricular lower extremities of the heart. The jacket is adapted to be secured to the heart. The jacket is adjustable on the heart to snugly conform to an external geometry of the heart and assume a maximum adjusted volume for the jacket to constrain circumferential expansion of the heart beyond the maximum adjusted volume during diastole and to permit unimpeded contraction of the heart during systole.

The cardiac constraint device further comprises an adjustment mechanism configured to alter the internal volume defined by the jacket. Preferably the adjustment mechanism is configured to alter the internal volume defined by the jacket after the jacket is secured to the heart. In one embodiment, the adjustment mechanism is configured to alter the internal volume defined by the jacket by varying the thickness of the jacket material defining the internal volume, for example, by constructing the jacket material at least in part from hygroscopic polymer or by incorporating a balloon catheter into the cardiac constraint device. Alternately, the adjustment mechanism may include a specialized material, such as a biodegradable material, a stimulus sensitive material, or a memory metal material. In another embodiment, the adjustment mechanism is configured to cinch the jacket material to effectively decrease said internal volume defined by said jacket, for example, using a stay element or a spring tensioning device.

The invention also provides a method for treating cardiac disease by surgically accessing a patient's heart, placing a cardiac restraining device around the patient's heart, adjusting the jacket to snugly conform to an external geometry of the heart to constrain circumferential expansion of the heart beyond a maximum adjusted volume, surgically closing access to the heart while leaving the jacket in place, and adjusting the internal volume defined by the jacket after the jacket is in place on the heart using an adjustment mechanism.

DETAILED DESCRIPTION OF THE INVENTION

1. Congestive Heart Disease

Figure 1A:
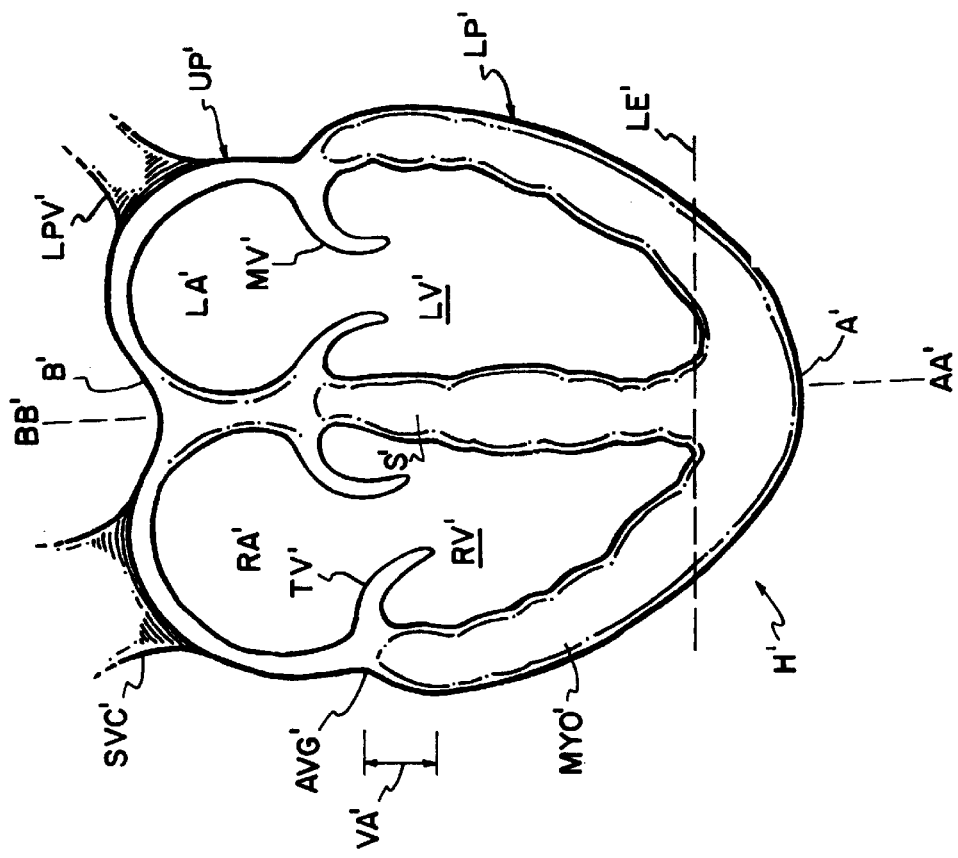
FIG. 1A is the view of FIG. 1 showing the heart during diastole.
Figure 1:
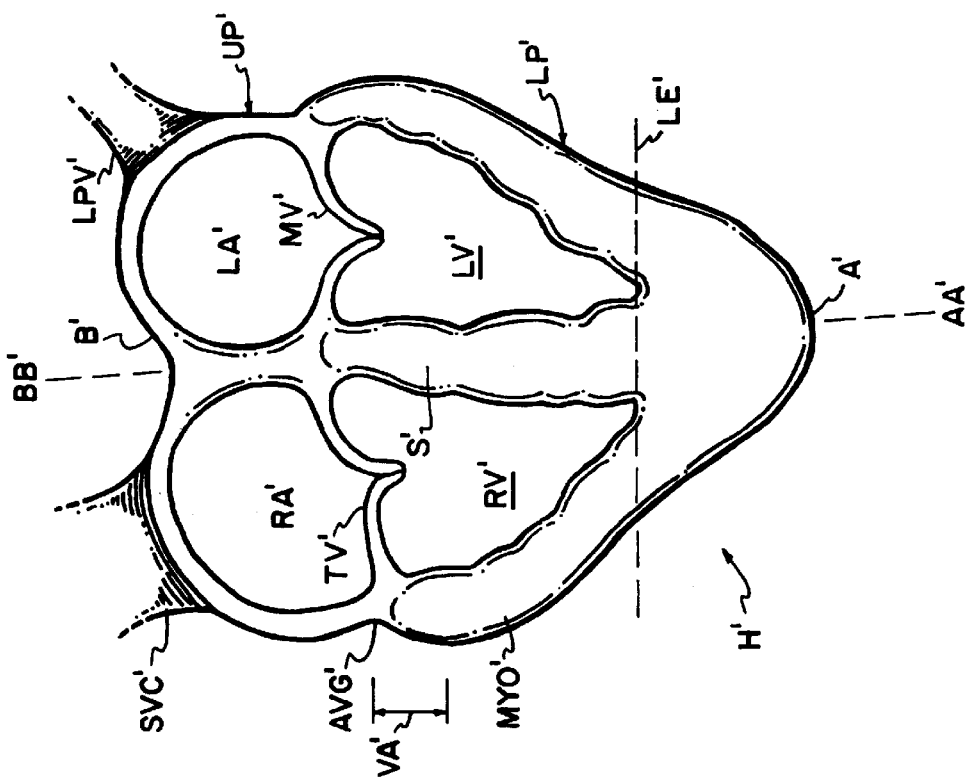
FIG. 1 is a schematic cross-sectional view of a normal, healthy human heart shown during systole.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The myocardium MYO' and septum S' define four internal heart chambers including a right atrium RA', a left atrium LA', a right ventricle RV' and a left ventricle LV'. The heart H' has a length measured along a longitudinal axis AA'–BB' from an upper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV', terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A-V groove AVG'. Extending away from the upper portion UP' are a plurality of major blood vessels communicating with the chambers RA', RV', LA', LV'. For ease of illustration, only the superior vena cava SVC' and a left pulmonary vein LPV' are shown as being representative.

The heart H' contains valves to regulate blood flow between the chambers RA', RV', LA', LV' and between the chambers and the major vessels (e.g., the superior vena cava SVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A-V groove AVG' and referred to as the valvular annulus VA'. The valves TV' and MV' open and close through the beating cycle of the heart H.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis AA'–BB').

The motion of the heart H' and the variation in the shape of the heart H' during contraction and expansion is complex. The amount of motion varies considerably throughout the heart H'. The motion includes a component which is parallel to the axis AA'–BB' (conveniently referred to as longitudinal expansion or contraction). The motion also includes a component perpendicular to the axis AA'–BB' (conveniently referred to as circumferential expansion or contraction).

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Figure 2B:
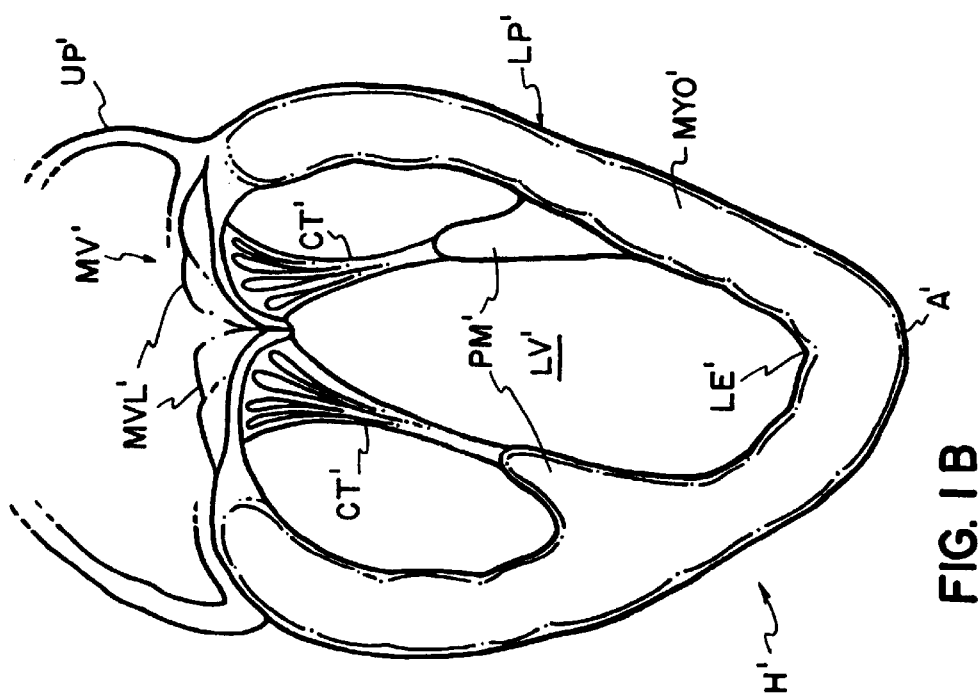
FIG. 2B is the view of FIG. 1B showing a diseased heart.
Figure 2A:
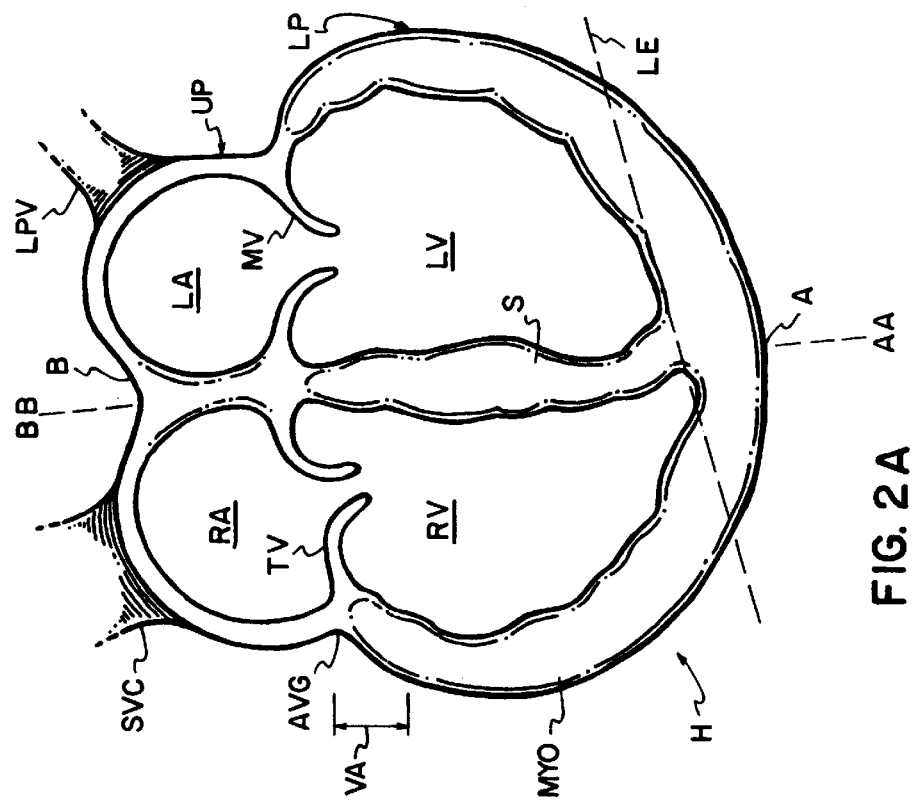
FIG. 2A is the view of FIG. 2 showing the heart during diastole.
Figure 2:
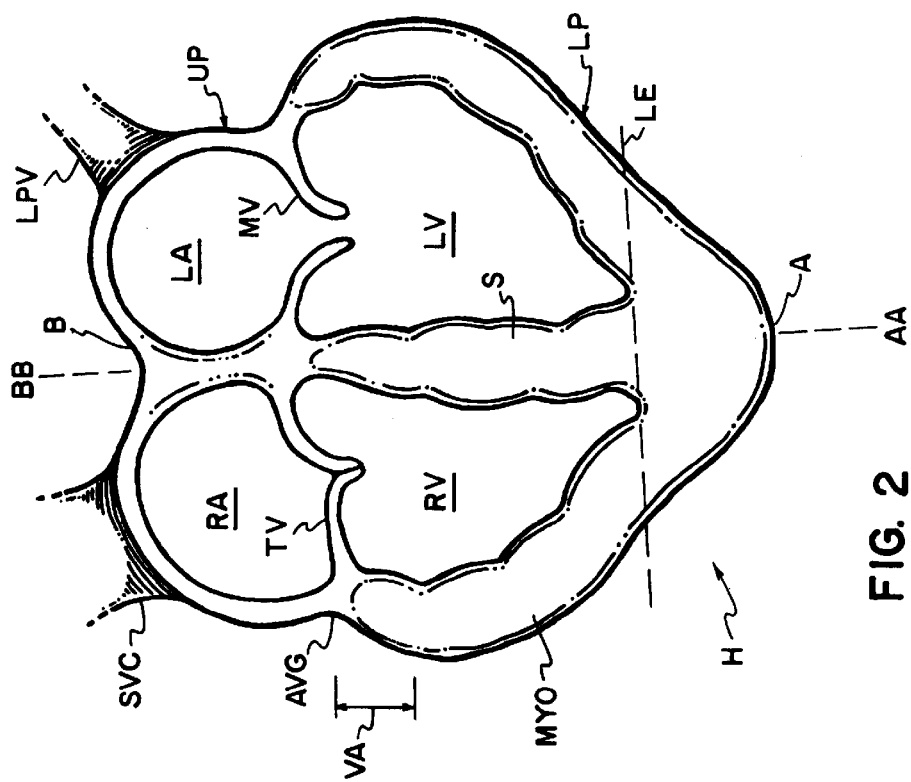
FIG. 2 is a schematic cross-sectional view of a diseased human heart shown during systole.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H bulges outwardly between the apex A and the A-V groove AVG. So deformed, the diseased heart H during systole (FIG. 2) resembles the healthy heart H' during diastole (FIG. 1A). During diastole (FIG: 2A), the deformation is even more extreme.

As a diseased heart H enlarges from the representation of FIGS. 1 and 1A to that of FIGS. 2 and 2A, the heart H becomes a progressively inefficient pump. Therefore, the heart H requires more energy to pump the same amount of blood. Continued progression of the disease results in the heart H being unable to supply adequate blood to the patient's body and the patient becomes symptomatic.

For ease of illustration, the progression of congestive heart disease has been illustrated and described with reference to a progressive enlargement of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close (as illustrated by the mitral valve MV in FIG. 2A). Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H. This is best described with reference to FIGS. 1B and 2B.

Figure 1B:
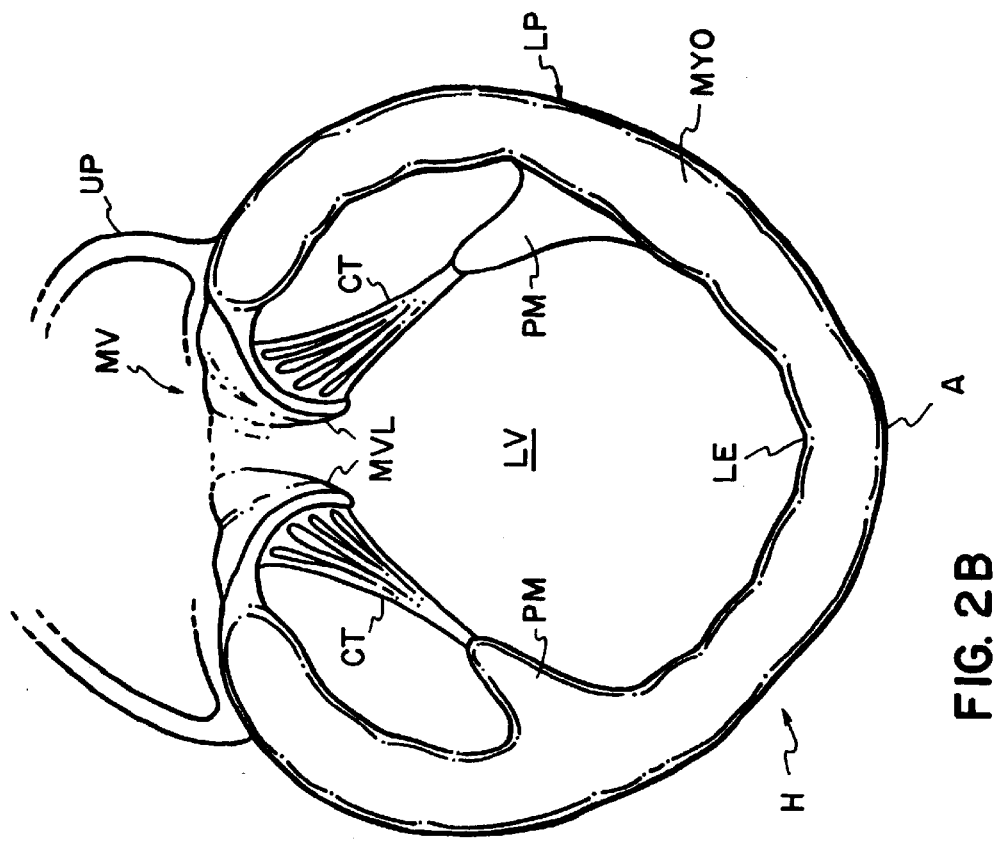
FIG. 1B is a view of a left ventricle of a healthy heart as viewed from a septum and showing a mitral valve.

FIGS. 1B and 2B show a healthy and diseased heart, respectively, left ventricle LV', LV during systole as viewed from the septum (not shown in FIGS. 1B and 2B). In a healthy heart H', the leaflets MVL' of the mitral valve MV' are urged closed by left ventricular pressure. The papillary muscles PM', PM are connected to the heart wall MYO', MYO, near the lower ventricular extremities LE', LE. The papillary muscles PM', PM pull on the leaflets MVL', MVL via connecting chordae tendineae CT', CT. Pull of the leaflets by the papillary muscles functions to prevent valve leakage in the normal heart by holding the valve leaflets in a closed position during systole. In the significantly diseased heart H, the leaflets of the mitral valve may not close sufficiently to prevent regurgitation of blood from the ventricle LV to the atrium during systole.

As shown in FIG. 1B, the geometry of the healthy heart H' is such that the myocardium MYO', papillary muscles PM' and chordae tendineae CT' cooperate to permit the mitral valve MV' to fully close. However, when the myocardium MYO bulges outwardly in the diseased heart H (FIG. 2B), the bulging results in displacement of the papillary muscles PM. This displacement acts to pull the leaflets MVL to a displaced position such that the mitral valve cannot fully close.

Having described the characteristics and problems of congestive heart disease, the treatment method and apparatus of the present invention will now be described.

2. Cardiac Constraint Device

To facilitate a better understanding of the present invention, a cardiac constraint device will be provided. The cardiac constraint device is more fully described in commonly assigned PCT Published Application No. WO 00/02500, the disclosure of which is hereby incorporated by reference herein. In the drawings, similar elements are labeled similarly throughout.

In general, the device of the invention comprises a jacket configured to surround the myocardium MYO. As used herein, "surround" means that jacket provides reduced expansion of the heart wall at end diastole by applying constraining surfaces at least at diametrically opposing aspects of the heart. In some preferred embodiments disclosed herein, the diametrically opposed surfaces are interconnected, for example, by a continuous material that can substantially encircle the external surface of the heart.

With reference now to FIGS. 3, 3A, 4 and 4A, the device of the present invention is shown as a jacket 10 of flexible, biologically compatible material. As used herein, the term "biologically compatible material" refers to material that does not adversely affect the surrounding tissue, for example, by eliciting an excessive or injurious rejection response, inflammation, infarction, necrosis, etc.

The jacket 10 is an enclosed material having upper and lower ends 12, 14. The jacket 10, 10' defines an internal volume 16, 16' which is completely enclosed but for the open ends 12, 12' and 14'. In the embodiment of FIG. 3, lower end 14 is closed. In the embodiment of FIG. 4, lower end 14' is open. In both embodiments, upper ends 12, 12' are open. Throughout this description, the embodiment of FIG. 3 will be discussed. Elements in common between the embodiments of FIGS. 3 and 4 are numbered identically with the addition of an apostrophe to distinguish the second embodiment and such elements need not be separately discussed.

The jacket 10 is dimensioned with respect to a heart H to be treated. Specifically, the jacket 10 is sized for the heart H to be constrained within the volume 16. The jacket 10 can be slipped around the heart H. The jacket 10 has a length L between the upper and lower ends 12, 14 sufficient for the jacket 10 to constrain the lower portion LP. The upper end 12 of the jacket 10 extends at least to the valvular annulus VA and further extends to the lower portion LP to constrain at least the lower ventricular extremities LE.

Generally, the jacket 10 is adjusted to a snug fit encompassing the external volume heart 10 during diastole such that the jacket 10 constrains enlargement of the heart H during diastole without significantly assisting contraction during systole. The amount of assistance during systole can be characterized by the pressure exerted by the jacket 10 on the heart H during systole. A jacket 10 that does not significantly assist contraction during systole will not exert significant pressure on the heart H at completion of systolic contraction.

Since enlargement of the lower portion LP is typically most troublesome, in a preferred embodiment, the jacket 10 is sized so that the upper end 12 can reside in the A-V groove AVG. Where it is desired to constrain enlargement of the upper portion UP, the jacket 10 may be extended to cover the upper portion UP.

Sizing the jacket 10 for the upper end 12 to terminate at the A-V groove AVG is desirable for a number of reasons. First, the groove AVG is a readily identifiable anatomical feature to assist a surgeon in placing the jacket 10. By placing the upper end 12 in the A-V groove AVG, the surgeon is assured the jacket 10 will provide sufficient constraint at the valvular annulus VA. The A-V groove AVG and the major vessels act as natural stops for placement of the jacket 10 while assuring coverage of the valvular annulus VA. Using such features as natural stops is particularly beneficial in minimally invasive surgeries where a surgeon's vision may be obscured or limited.

When the parietal pericardium is opened, the lower portion LP is free of obstructions for applying the jacket 10 over the apex A. If, however, the parietal pericardium is intact, the diaphragmatic attachment to the parietal pericardium inhibits application of the jacket over the apex A of the heart. In this situation, the jacket can be opened along a line extending from the upper end 12' to the lower end 14' of jacket 10'. The jacket can then be applied around the pericardial surface of the heart and the opposing edges of the opened line secured together after placed on the heart. Systems for securing the opposing edges are disclosed in, for example, U.S. Pat. No. 5,702,343 (corresponding to WO 98/14136), the entire disclosure of both applications being incorporated herein by reference. The lower end 14' can then be secured to the diaphragm or associated tissues using, for example, sutures, staples, etc.

Figure 3A:
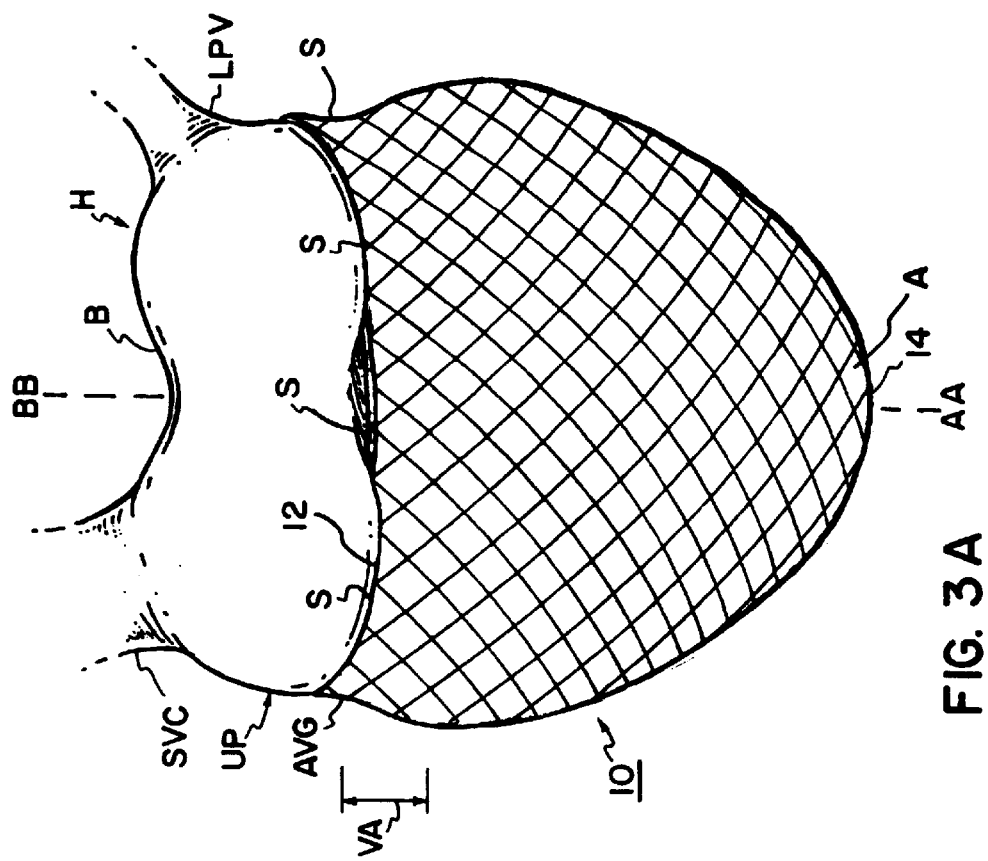
FIG. 3A is a side elevation view of a diseased heart in diastole with the device of FIG. 3 in place.
Figure 3:
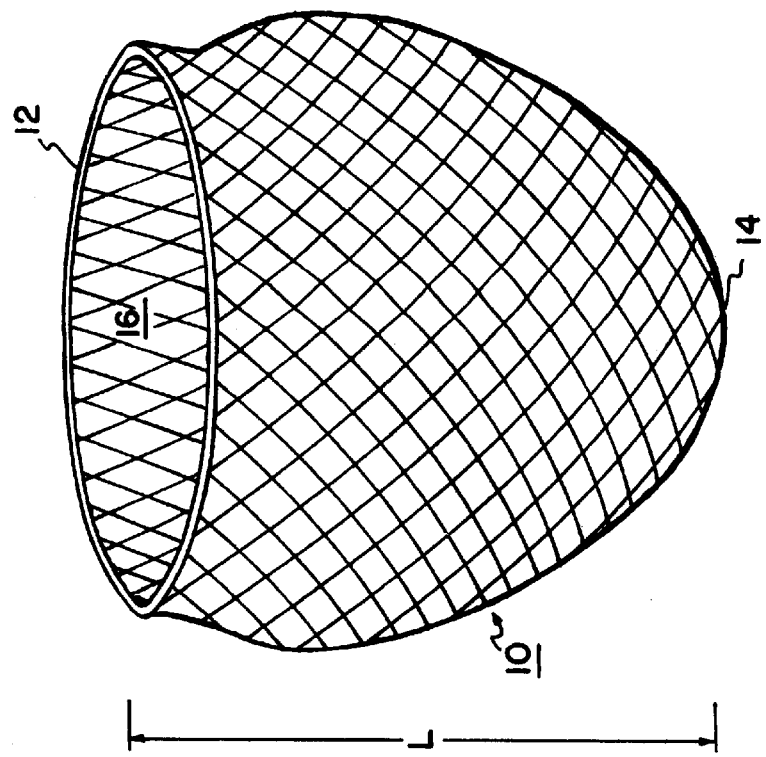
FIG. 3 is a perspective view of a first embodiment of a cardiac constraint device according to the present invention.
Figure 4A:
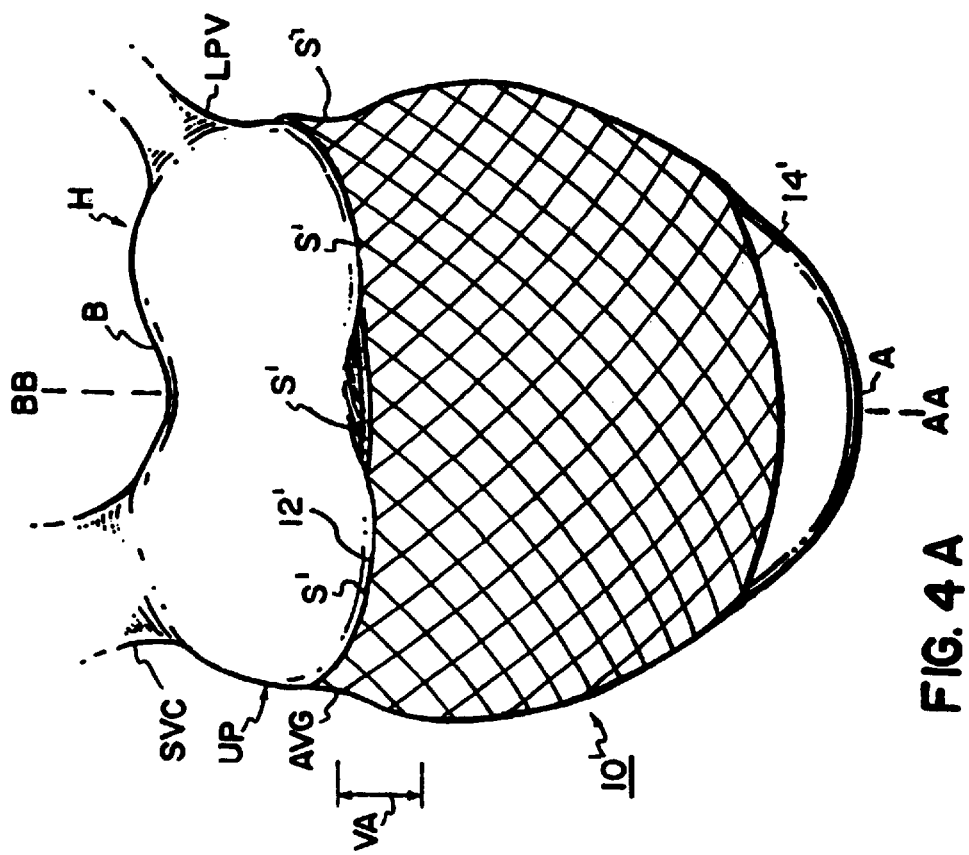
FIG. 4A is a side elevation view of a diseased heart in diastole with the device of FIG. 4 in place.
Figure 4:
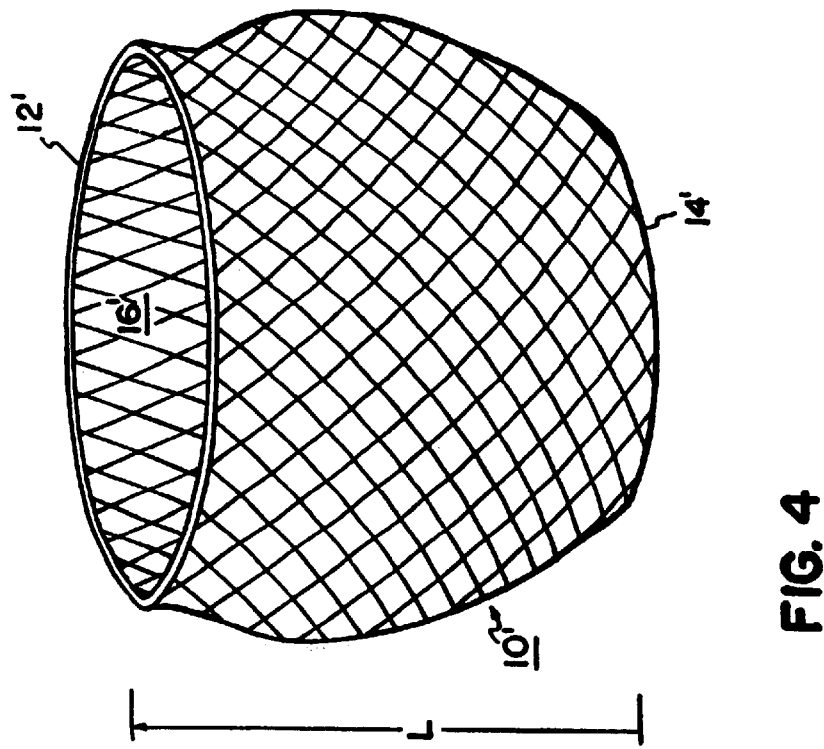
FIG. 4 is a perspective view of a second embodiment of a cardiac constraint device according to the present invention.

In the embodiment of FIGS. 3 and 3A, the lower end 14 is closed and the length L is sized for the apex A of the heart H to be received within the lower end 14 when the upper end 12 is placed at the A-V groove AVG. In the embodiment of FIGS. 4 and 4A, the lower end 14' is open and the length L' is sized for the apex A of the heart H to protrude beyond the lower end 14' when the upper end 12' is placed at the A-V groove AVG. The length L' is sized so that the lower end 14' extends beyond the lower ventricular extremities LE such that in both of jackets 10, 10', the myocardium MYO surrounding the ventricles RV, LV is in direct opposition to material of the jacket 10, 10'. Such placement is desirable for the jacket 10, 10' to present a constraint against enlargement of the ventricular walls of the heart H.

After the jacket 10 is positioned on the heart H as described above, the jacket 10 is secured to the heart. Preferably, the jacket 10 is secured to the heart H through sutures. The jacket 10 is sutured to the heart H at suture locations S circumferentially spaced along the upper end 12. While a surgeon may elect to add additional suture locations to prevent shifting of the jacket 10 after placement, the number of such locations S is preferably limited so that the jacket 10 does not restrict contraction of the heart H during systole.

Figure 5:
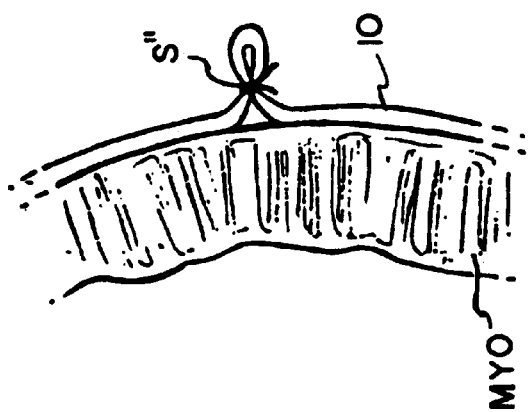
FIG. 5 is a cross-sectional view of a device of the present invention overlying a myocardium and with the material of the device gathered for a snug fit.

To permit the jacket 10 to be easily placed on the heart H, the volume and shape of the jacket 10 are larger than the lower portion LP during diastole. So sized, the jacket 10 may be easily slipped around the heart H. Once placed, the jacket's volume and shape are adjusted for the jacket 10 to snugly conform to the external geometry of the heart H during diastole. Such sizing is easily accomplished due to the knit construction of the jacket 10. For example, excess material of the jacket 10 can be gathered and sutured S" (FIG. 5) to reduce the volume of the jacket 10 and conform the jacket 10 to the shape of the heart H during diastole. Such shape represents a maximum adjusted volume. The jacket 10 constrains enlargement of the heart H beyond the maximum adjusted volume while preventing restricted contraction of the heart H during systole. As an alternative to gathering of FIG. 5, the jacket 10 can be provided with other ways of adjusting volume. For example, as disclosed in U.S. Pat. No. 5,702,343 (WO 98/14136), the jacket can be provided with a slot. The edges of the slot can be drawn together to reduce the volume of the jacket.

The volume of the jacket can be adjusted prior to, during, or after application of the device to the heart. In one embodiment, the heart is treated with a therapeutic agent, such as a drug to decrease the size of the heart, prior to application of the jacket. In this embodiment, the therapeutic agent acts to reduce the overall size of the heart prior to surgery, and the jacket is thereafter applied to the reduced heart. Alternatively, the present invention can be used to reduce heart size at the time of placement in addition to preventing further enlargement. For example, the device can be placed on the heart and sized snugly to urge the heart to a reduced size. More preferably, the heart size can be reduced at the time of jacket placement through drugs, for example dobutamine, dopamine or epinephrine or any other positive inotropic agents, or surgical procedure to reduce the heart size. The jacket of the present invention is then snugly placed on the reduced sized heart and prevents enlargement beyond the reduced size.

The jacket 10 is adjusted to a snug fit on the heart H during diastole. Care is taken to avoid tightening the jacket 10 too much such that cardiac function is impaired. During diastole, the left ventricle LV fills with blood. If the jacket 10 is too tight, the left ventricle LV may not adequately expand and left ventricular pressure will rise. During the fitting of the jacket 10, the surgeon can monitor left ventricular pressure. For example, a well-known technique for monitoring so-called pulmonary wedge pressure uses a catheter placed in the pulmonary artery. The wedge pressure provides an indication of filling pressure in the left atrium LA and left ventricle LV. While minor increases in pressure (e.g., 2 mm Hg–3 mm Hg) can be tolerated, the jacket 10 is snugly fit on the heart H but not so tight as to cause a significant increase in left ventricular pressure during diastole.

The jacket 10 can be used in early stages of congestive heart disease. For patients facing heart enlargement due to viral infection, the jacket 10 permits constraint of the heart H for a sufficient time to permit the viral infection to pass. In addition to preventing further heart enlargement, the jacket 10 treats valvular disorders by constraining circumferential enlargement of the valvular annulus and deformation of the ventricular walls.

3. Jacket Material Generally

Preferably the jacket 10 is constructed from a compliant, biocompatible material. As used herein, the term "compliant" refers to a material that can expand in response to a force. "Compliance" refers to the displacement per a unit load for a material. "Elasticity" refers to the ability of the deformed material to return to its initial state after the deforming load is removed.

While-the jacket 10 is expandable due to its knit pattern, preferably the fibers 20 of the knit are non-expandable. While all materials expand at least a small amount, the individual fibers 20 do not substantially stretch in response to force. In response to the low pressures of the heart H during diastole, the fibers 20 are generally inelastic. In a preferred embodiment, the Jacket material is 70 Denier polyester. While polyester is presently preferred, other suitable materials include polytetrafluoroethylene (PTFE), expanded PTFE (ePTFE), polypropylene and stainless steel.

Figure 6:
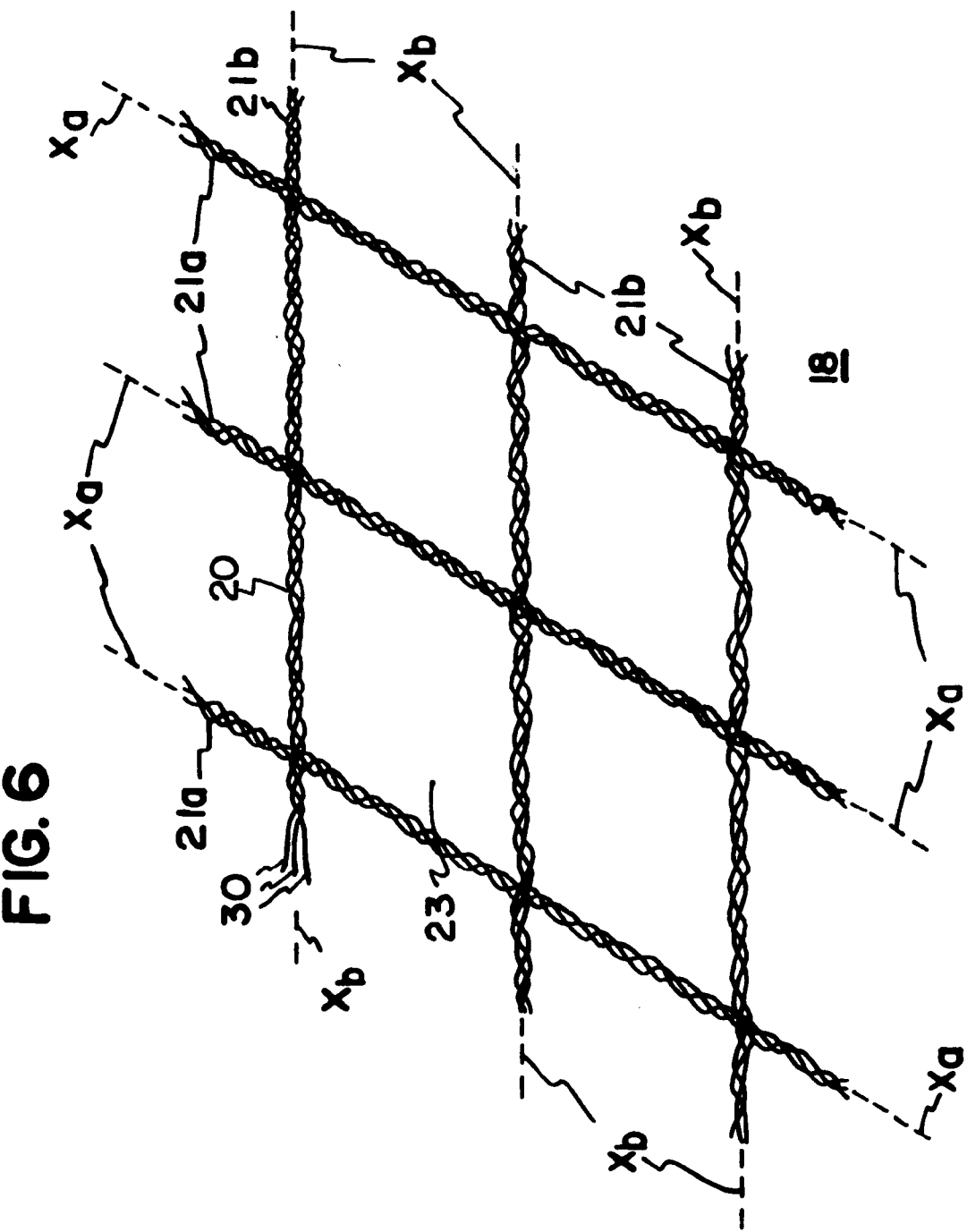
FIG. 6 is an enlarged view of a knit construction of the device of the present invention in a rest state.

Preferably, the knit is a so-called "Atlas knit" well known in the fabric industry. The Atlas knit is described in Paling, *Warp Knitting Technology,* p. 111, Columbine Press (Publishers) Ltd., Buxton, Great Britain (1970). The Atlas knit is a knit of fibers 20 having directional expansion properties. As shown in FIG. 6, the intertwined fibers 20 include a plurality of longitudinally extending filaments 30, wherein opposing surfaces of said multi-filament fibers 20 define a cell structure. The fibers 20 of the fabric 18 are woven into two sets of fiber strands 21a, 21b having longitudinal axes $X_a$ and $X_b$. The strands 21a, 21b are interlaced to form the fabric 18 with strands 21a generally parallel and spaced-apart and with strands 21b generally parallel and spaced-apart.

Figure 7:
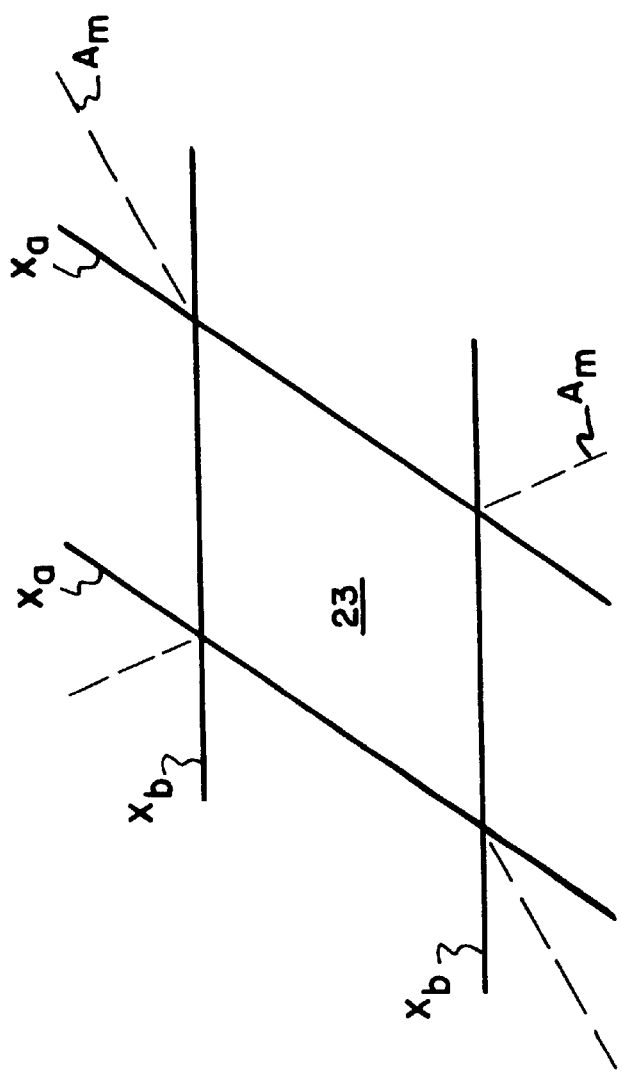
FIG. 7 is a schematic view of the material of FIG. 6.

For ease of illustration, fabric 18 is schematically shown in FIG. 7 with the axis of the strands 21a, 21b only being shown. The strands 21a, 21b are interlaced with the axes $X_a$ and $X_b$ defining a diamond-shaped open cell 23 having diagonal axes $A_m$. In a preferred embodiment, the axes $A_m$ are 3 mm–5 mm in length when the fabric 18 is at rest and not stretched. The fabric 18 can stretch in response to a force. For any given force, the fabric 18 stretches most when the force is applied parallel to the diagonal axes $A_m$. The fabric 18 stretches least when the force is applied parallel to the strand axes $X_a$ and $X_b$. The jacket 10 is constructed for the material of the knit to be directionally aligned for a diagonal axis $A_m$ to be parallel to the heart's longitudinal axis AA–BB The knit material has numerous advantages. Such a material is flexible to permit unrestricted movement of the heart H (other than the desired constraint on circumferential expansion). The material is open defining a plurality of interstitial spaces for fluid permeability as well as minimizing the amount of surface area of direct contact between the heart H and the material of the jacket 10 (thereby minimizing areas of irritation or abrasion) to minimize fibrosis and scar tissue.

The open areas of the knit construction also allows for electrical connection between the heart and surrounding tissue for passage of electrical current to and from the heart. For example, although the knit material is an electrical insulator, the open knit construction is sufficiently electrically permeable to permit the use of trans-chest defibrillation of the heart. Also, the open, flexible construction permits passage of electrical elements (e.g., pacer leads) through the jacket. Additionally, the open construction permits other procedures, e.g., coronary bypass, to be performed without removal of the jacket.

A large open area for cells 23 is desirable to minimize the amount of surface area of the heart H in contact with the material of the jacket 10 (thereby reducing fibrosis). However, if the cell area 23 is too large, localized aneurysm can form. Also, a strand 21a, 21b can overly a coronary vessel with sufficient force to partially block the vessel. A smaller cell size increases the number of strands thereby decreasing the restricting force per strand. In a preferred embodiment, the cell area of cells in a particular row directly correlates with a cross-sectional circumferential dimension of the heart that the row of cells surrounds relative to other cross-sectional circumferential dimensions. That is, the greater the cross-sectional circumferential dimension, the greater the area of the cells in the row of cells directly overlying that cross-sectional circumferential dimension. By "correlating" cell area with cross-sectional circumferential dimension of the heart, the cell area is determined as a function of the cross-sectional circumferential dimension of the heart. The cell area is determined so that when the weave material is applied to the heart or is shaped into a jacket and applied to the heart, each cell can widen sufficiently to provide desirable cardiac constraint. Thus, the cell area will be smaller for cells in a row applied over a region of the heart that has a smaller cross-sectional circumferential dimension than the cell area of cells in a row applied over a region of the heart having a larger cross-sectional circumferential dimension. The appropriate maximum cell area may be, for example, 1 to 100 $mm^2$, typically 1 to 25 $mm^2$, more typically 3 to 9 $mm^2$. The maximum cell area is the area of a cell 23 after the material of the jacket 10 is fully stretched and adjusted to the maximum adjusted volume on the heart H as previously described.

The fabric 18 is preferably tear and run resistant. In the event of a material defect or inadvertent tear, such a defect or tear is restricted from propagation by reason of the knit construction.

With the foregoing, a device and method have been taught to treat cardiac disease. The jacket 10 constrains further undesirable circumferential enlargement of the heart while not impeding other motion of the heart H. With the benefits of the present teachings, numerous modifications are possible. For example, the jacket 10 need not be directly applied to the epicardium (i.e., outer surface of the myocardium) but could be placed over the parietal pericardium. Further, an anti-fibrosis lining (e.g., a PTFE lining) could be placed between the heart H and the jacket 10. Alternatively, the fibers 20 can be coated with PTFE.

The jacket 10 is low-cost, easy to place and secure, and is susceptible to use in minimally invasive procedures. The thin, flexible fabric 18 permits the jacket 10 to be collapsed and passed through a small diameter tube in a minimally invasive procedure.

The jacket 10, including the knit construction, freely permits longitudinal and circumferential contraction of the heart H (necessary for heart function). Unlike a solid wrap (such as a muscle wrap in a cardiomyoplasty procedure), the fabric 18 does not impede cardiac contraction. After fitting, the jacket 10 is inelastic to prevent further heart enlargement while permitting unrestricted inward movement of the ventricular walls. Because the jacket 10 is not constructed from an elastomeric material, it does not substantially assist the heart during systolic contraction.

The open cell structure permits access to coronary vessels for bypass procedures subsequent to placement of the jacket 10. Also, in cardiomyoplasty, the latissimus dorsi muscle has a variable and large thickness (ranging from about 1 mm to 1 cm). The material of the jacket 10 is uniformly thin (less than 1 mm thick). The thin wall construction is less susceptible to fibrosis and minimizes interference with cardiac contractile function.

4. Adjustment Mechanism

Chronic heart failure is a dynamic syndrome in which cardiac chambers may change in size and shape. It has been found that use of a cardiac restraining device, such as the above-described jacket, may stop cardiac dilation or even, under some circumstances, reverse cardiac dilation. Preferably, beneficial reverse remodeling of the heart reduces the maximum cardiac volume of a diseased heart.

If beneficial reverse remodeling of cardiac physiology occurs following implantation of a cardiac restraining device, such as the above-described jacket 10, it may be desirable to have a jacket 10 that can be adjusted to respond to the change in cardiac size, or promote the change in cardiac size, for example, by changing or reducing internal volume defined by the jacket 10. A cardiac support device ideally would have a capacity to contract in size, so that it maintains intimate contact with the cardiac surface and continues to provide a finite limit to cardiac expansion and provides support to encourage reverse remodeling.

The invention provides a jacket 10 that defines an internal volume 16 that can be adjusted such that the jacket 10 is capable of maintaining intimate contact with the external cardiac surface, even if the cardiac volume changes (i.e., increases or decreases) following implantation of the jacket 10. The invention provides a cardiac constraint device that includes a jacket 10 an adjustment mechanism which allows the jacket 10 to be adjusted in size either prior to or after implantation. The jacket 10 may also be adjusted to actively encourage reduction in cardiac volume by reducing the maximum adjusted volume of the heart H. Preferably, the cardiac restraint device includes an adjustment mechanism which is capable of increasing and/or decreasing the internal volume 16 defined by the jacket 10.

As used herein, the term adjustment mechanism refers to an apparatus or system that is adapted, configured and capable of altering the size and/or shape of the above-described jacket 10, particularly the internal volume 16 defined by the jacket 10. Many adjustment mechanisms are possible. Although some adjustment mechanisms will be discussed in detail below, a cursory overview will be provided at this time.

Figure 9A:
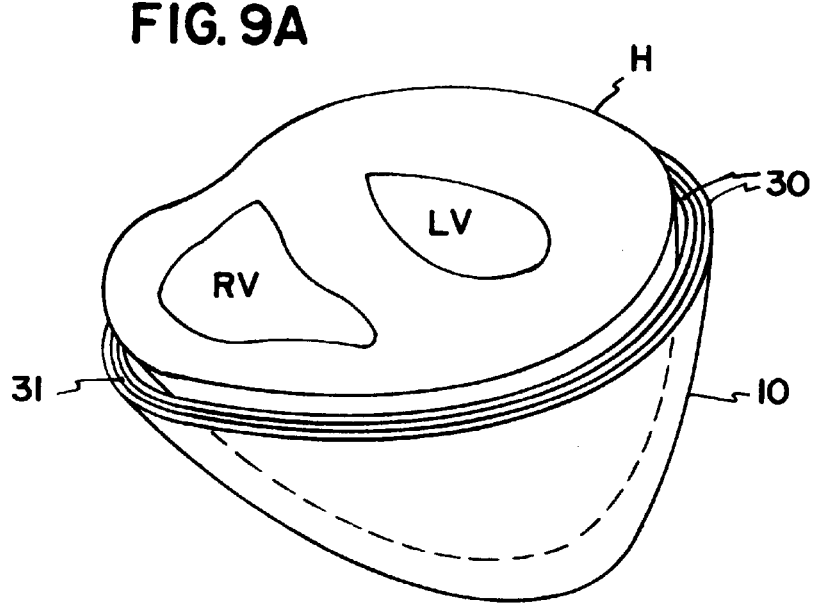
FIG. 9A is a transverse sectional view of a tensioned cardiac constraint device according to one embodiment.
Figure 9B:
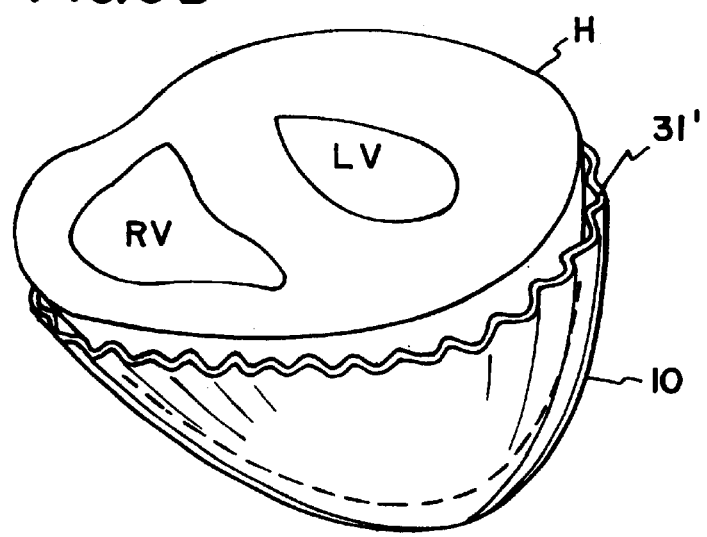
FIG. 9B is a transverse sectional view of the device of FIG. 9A in a relaxed state.

One type of adjustment mechanism varies the thickness of the cardiac constraint device to effectively decrease the internal volume 16 defined by the jacket 10. For example, the jacket 10 may be constructed using a hygroscopic polymer which causes the jacket 10 fibers to expand as fluids are absorbed from the surrounding tissue. Alternately, the cardiac constraint device may include a balloon catheter which can be expanded to effectively reduce the internal volume 16 defined by the jacket 10. Another type of adjustment mechanism cinches the jacket 10 material to effectively decrease the internal volume 16 defined by the jacket 10. For example, the adjustment mechanism may include a stay element and/or a spring tensioning device to pinch or draw together the material of the jacket 10. Alternately, the adjustment mechanism may include a specialized material, such as a stimulus sensitive material or a biodegradable material that causes the jacket 10 material to contract, thereby reducing the internal volume 16 defined by the jacket 10. A still further example is a jacket 10 which includes a biodegradable polymer matrix 30 in which a substrate structure 31 is embedded. Preferably the substrate structure 31 is formed using a material (e.g., a shape-changing memory metal such as nitinol) which is tensioned (to define a volume) prior to incorporation into the polymer matrix. Preferably, the tensioned structure 31 is sized for initial placement on the heart. (See FIG. 9A) Over time, the size of the heart is reduced (e.g., by reverse remodeling) and the supporting polymer matrix 30 is degraded. Degradation of the polymer matrix 31 relieves the tension on the underlying structure 31' which is then free to relax. (See FIG. 9B) Preferably the relaxed structure 31' defines a reduced maximum volume (as compared to the tensioned structure) to encourage continued reverse remodeling of the heart. Other adjustment systems or mechanisms may include combinations of the above described mechanisms.

If desired, cardiac volume can be reduced prior to placement of the jacket 10 on the heart or at the time of jacket 10 placement by the administration of drugs (e.g., dobutamine, dopamine or epinephrine or any other positive inotropic agents) which reduce heart size. Alternately, cardiac volume can be reduced (prior to implantation or after implantation) by the temporary use of LVADs or chronic pacing. The jacket of the present invention is situated on the reduced sized heart to prevent enlargement beyond the reduced size.

Preferably the size of the jacket 10 is adjusted within about 1 to about 3 months after the jacket 10 is implanted, particularly for those devices in which fibrous ingrowth is allowed or promoted (stable fibrous ingrowth generally occurs approximately 3 months or less after implantation). However, the device may be adjusted after ingrowth (e.g., after 3 months). Preferably, if the jacket 10 is adjusted more than 3 months after implantation, the adjustment is performed slowly over time to allow time for remodeling of the fibrotic encapsulation of the jacket 10. Advantageously, a positive cardiac response to the reduced size is more likely to be favorable in response to a slow, gradual tensioning, as compared to a rapid decrease in size.

A. Fibrotic Encapsulation

After implantation of the cardiac constraint device such as the device of the invention, the fabric of the jacket 10 may become encapsulated by superficial fibrosis on the cardiac surface. Fibrotic attachment of the jacket 10 to the cardiac surface can encourage the jacket 10 to maintain intimate contact with the cardiac surface and thus "adjust" the internal volume 16 defined by the jacket 10 if the heart volume decreases after the jacket 10 is implanted. Thus, the fibrotic encapsulation may also limit the maximum cardiac volume. The fibrotic layer may even shrink over time, further contributing to therapy.

If fibrotic attachment is not established between the jacket 10 and the cardiac surface, a decrease in cardiac volume could ultimately result in a loose-fitting jacket 10 that may stimulate a thick late-stage fibrositic layer due to chronic abrasion of the jacket 10 on the cardiac surface or due to a build up of excessive fibrous tissue between the cardiac surface and the jacket.

Although fibrotic encapsulation may be generally beneficial in maintaining a reduced cardiac profile, fibrotic encapsulation of the jacket 10 may not maintain a reduced cardiac profile long-term. The fibrotic layer may gradually expand (similar to expansion of pericardium during congestive heart disease) until the maximum cardiac volume is constrained by the jacket 10.

B. Biodegradable Elements

In one embodiment, at least one biodegradable element, preferably a plurality of biodegradable elements, are incorporated into the jacket 10 to maintain a desired first internal volume 16 of the jacket 10. Preferably, the jacket 10 is designed such that, when the biodegradable element is removed or degraded, the internal volume 16 jacket 10 decreases to a pre-determined second internal volume 16. Consequently, as the biodegradable elements degrade in vivo, the internal volume 16 defined by the jacket 10 decreases.

As used herein, the term "biodegradable" means that the polymer will degrade over time by the action of enzymes, by hydrolytic action and/or by other similar mechanisms in the human body. Biodegradable may also refer to a material that is "bioerodible," meaning that the material will erode or degrade over time due, at least in part, to contact with substances found in the surrounding tissue fluids, cellular action and/or "bioabsorbable," meaning that the material will be broken down and absorbed within the human body, for example, by a cell, and a tissue.

The biodegradable elements can be incorporated into the jacket 10 as filaments 30 in the jacket 10 fibers 20, or as fibers 20 themselves. Alternately, a biodegradable matrix can be embedded in interstices between the filaments 30, fibers 20 and/or open cells 23 of the jacket 10 material. Other methods for incorporating biodegradable elements into the jacket 10 include placement of a pre-tensioned structure as previously described.

Suitable biodegradable elements include biodegradable synthetic polymers such as polylactides, polyglycolides, polycaprolactones, polyanhydrides, polyamides, polyurethanes, polyesteramides, polyorthoesters, polydioxanones, polyacetals, polyketals, polycarbonates, polyorthoesters, polyphosphazenes, polyhydroxybutyrates, polyhydroxyvalerates, polyalkylene oxalates, polyalkylene succinates, poly(methyl vinyl ether), poly(maleic anhydride), poly(amino acids) and copolymers, combinations or mixtures thereof. Suitable biodegradable elements also include biodegradable natural polymers such as those derived from corn, wheat, potato, sorghums, tapioca, rice, arrow root, sago, soybean, pea, sunflower, peanut, gelatin, milk, and eggs, for example. Natural polymers generally include polysaccharides, proteins, poly(nucleic acids), poly(amino acids), and lipids. Polysaccharides include gums, starch, cellulose, etc. As used herein, the term "oligosaccharide" denotes a sugar polymer of from 3 to 15 units. A sugar polymer having more than 10 units referred to as a "polysaccharide." Suitable proteins that may be utilized in the present invention include egg proteins, milk proteins, animal proteins, vegetable proteins and cereal proteins.

C. Hygroscopic Polymers

In an alternate embodiment, the jacket 10, or a portion thereof, is constructed from a hygroscopic material. According to this embodiment, the hygroscopic material sequesters water from surrounding tissue after the jacket is implanted and thus expands. Expansion of the hygroscopic material reduces the internal volume 16 of the jacket 10 such that the internal surface of the jacket 10 can maintain intimate contact with the cardiac surface, even if the cardiac volume decreases.

Hygroscopic material can be incorporated into the cardiac constraint device as filaments 30 in the jacket 10 fibers 20, or as fibers 20 themselves (See, e.g., FIG. 6). Alternately, a hygroscopic matrix can be embedded in interstices between the filaments 30, fibers 20 and/or open cells 23 of the jacket 10 material. Other methods for incorporating hygroscopic material into the device include applying a hygroscopic polymer coating to the filaments 30 and/or fibers 20 of the jacket 10. A liner constructed using at least some amount of hygroscopic polymer can be formed which substantially conforms to the internal surface of the jacket 10.

Examples of hygroscopic polymer(s) include natural polymers such as glycosaminoglycans, for example, hyaluronic acid, chondroitin sulfate, and cellulose and synthetic polymers, such as hydrogels, poly(vinyl alcohol), poly(2-hydroxyethylmethacrylate), polyethylene oxide.

D. Stimulus Sensitive Material

In another embodiment, the jacket 10 is constructed, in its entirety, or in part, from a material that changes shape and/or size in response to a stimulus. Examples of stimuli include a temperature change (e.g., room temperature to body temperature), electric current, ultrasound, radiofrequency (rf), microwave energy, or any other stimulus that could elicit a change in device shape or size.

A stimulus sensitive material can be incorporated into the device as a filament 30 in the jacket 10 fibers 20, or as a fiber 20 of the jacket 10 material. The stimulus sensitive material can be included in the jacket 10 as a stay element in the form of a hoop, coil, V or W shaped element, or a continuous zig-zag shape oriented circumferentially about the jacket 10.

The size of a jacket 10 (or the internal volume 16 defined by the jacket) constructed from (at least in part) a stimulus-sensitive material can be modified by applying energy (i.e. in the form of electric current, ultrasound, radio frequency, or microwave energy) to the jacket 10. In one embodiment, the size of the jacket 10 (or the internal volume 16 of the jacket 10) can be incrementally modified by applying a specified quantity of energy multiple times. In another embodiment, the energy is applied using a pacemaker (whether or not the pacemaker is also implanted to control cardiac rhythm).

Polyvinylidine fluoride (PVDF), a piezoelectric material, is an example of a stimulus-sensitive material. In one embodiment, the jacket 10 is constructed, in part or in its entirety, from a piezoelectric material such as PVDF. In this embodiment, the shape and/or size of the jacket can be altered by the application of a low level electric current. Other stimulus sensitive materials include shape memory alloy elements, such as nitinol.

E. Stay Elements

Figure 8:
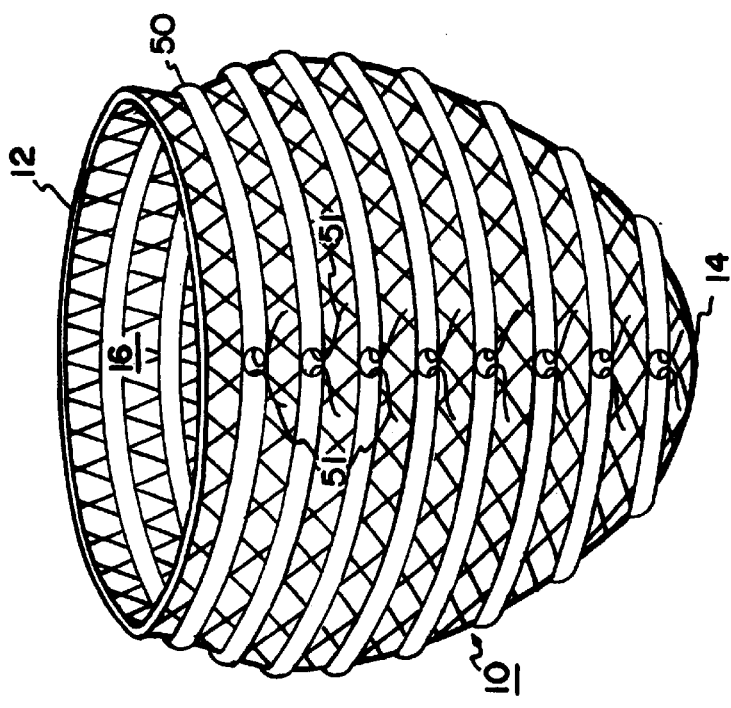
FIG. 8 is a perspective view of an alternate embodiment of a cardiac constraint device according to the present invention.

In another embodiment, stay elements 51, for example, bands, strings or ligatures, are incorporated into the cardiac constraint device. Preferably, the stay elements 51 are positioned circumferentially around the jacket 10 (as shown in FIG. 8). However, it may be desirable in some instances to align the stay elements 51 with the vertical axis AA'–BB' of the heart H or to position the stay elements 51 obliquely around the jacket 10. The stay elements 51 are preferably positioned within a receptacle 50 placed on the outer surface of the jacket 10. The receptacle 50 may be configured as a series of loops (not shown) or an elongate channel or sleeve of material. The receptacle 50 can orient the stay elements 51 in an essentially linear position, or the receptacle 50 can orient the stay elements 51 in a variety of configurations, such as a zig-zag configuration, a sinusoid wave configuration or a square wave configuration.

In this embodiment, the jacket 10 positions the stay elements 51 and/or the receptacle 50 on the heart H in the desired location and orientation and the stay elements 51 and/or the jacket 10 prevent the heart H from expanding.

In one embodiment, the jacket 10, stay elements 51 and receptacle 50 are constructed from a biocompatible non-biodegradable material. As used herein, the term "non-biodegradable" material refers to material that does not appreciably degrade over an extended period. Examples of non-biodegradable polymers include non-biodegradable polyester and PTFE.

Alternately, the jacket 10 is constructed from a biodegradable material while the stay elements 51 and the receptacles 50 are constructed from a non-biodegradable material. In this embodiment, the stay elements 51 are preferably housed within a non-biodegradable sleeve-like receptacle 50 that is attached to the jacket 10. Over time, the biodegradable jacket 10 degrades and the receptacles 50 housing the stay elements 51 become affixed to the epicardial surface as a result of fibrotic encapsulation and ingrowth.

The receptacle 50 may be constructed from either a porous material or a non-porous material. Preferably, the porous material of the sleeve-like receptacle 50 is constructed such that host tissue is only capable of growing a limited depth into the receptacle 50 material, thus keeping the interior surface of the receptacle 50 and stay elements 51 free from host tissue. For example, a material with pores large enough for cells to enter may form the exterior surface of the receptacle, and the internal surface of the receptacle may be lined with a material having pores too small for cells to pass through. Because the inner surface of the receptacle 50, and the stay elements 51 remain free of fibrous ingrowth, the stay elements 51 are easily adjusted after implantation. The tension of the stay elements 51 can be adjusted using simple knots, or a more sophisticated mechanism such as a ratchet mechanism, a balloon catheter (described below), or a stimulus sensitive material, to allow fine-tuning of the stay element 51 tension.

The above-described jacket 10 incorporating stay elements 51 can be adjusted prior to or after the jacket 10 is implanted (e.g., following closure of the patient at the end of surgery). For example, a special instrumentation may be provided for contacting the stay elements 51 through a minimally invasive procedure. Alternately, a motor, or other mechanical device may be implanted which is capable of tightening the stay elements 51 following implantation. Alternately, the stay elements 51 may be constructed using a stimulus sensitive material, as described above, such as PVDF or Nitinol.

F. Balloon Catheter

In another embodiment, an inflatable balloon catheter 60 is incorporated into the cardiac constraint device. A single balloon catheter 60 or multiple balloon catheters can be used. In one embodiment, the jacket 10 includes at least one balloon catheter 60 positioned along the internal surface of the jacket 10 and oriented parallel to axis AA'–BB' of the heart H and at least one, preferably a plurality, of stay elements 51 positioned circumferentially around the jacket 10 and balloon catheter 60. Inflation of the balloon 60 increases the tension of the stay elements 51 and thereby effectively reduces the internal volume 16 defined by the jacket 10. After implantation of the jacket 10, the balloon catheter 60 can be accessed using a connector implanted just beneath the patient's skin at a convenient location. The connector can be implanted, before, after or at the time the jacket 10 is implanted on heart H. Alternately, the balloon catheter 60 can be positioned circumferentially along the interior surface of the jacket 10 or in pre-determined locations on the interior surface of the jacket 10.

G. Spring Tensioning Mechanism

In another embodiment, a spring tensioning device is incorporated into the cardiac constraint device. At the time the device is implanted, the spring is maintained under tension by a suitable tension-lock mechanism. At a desired time after the device is implanted, the tension-lock mechanism is "tripped" and the spring-tension energy and tension is transferred from the spring to the jacket 10, resulting in reduction in the internal volume 16 defined by the jacket 10, and relaxation of the spring. Internal, external and/or minimally invasive tripping mechanisms can be used. An example of an external tripping mechanism is a signaling device such as an magnet. A minimally invasive tripping mechanism can be a tool that is inserted through an opening in the patient to trip the tension-lock mechanism.

H. Elastic Tensioning Mechanism

Figure 10:
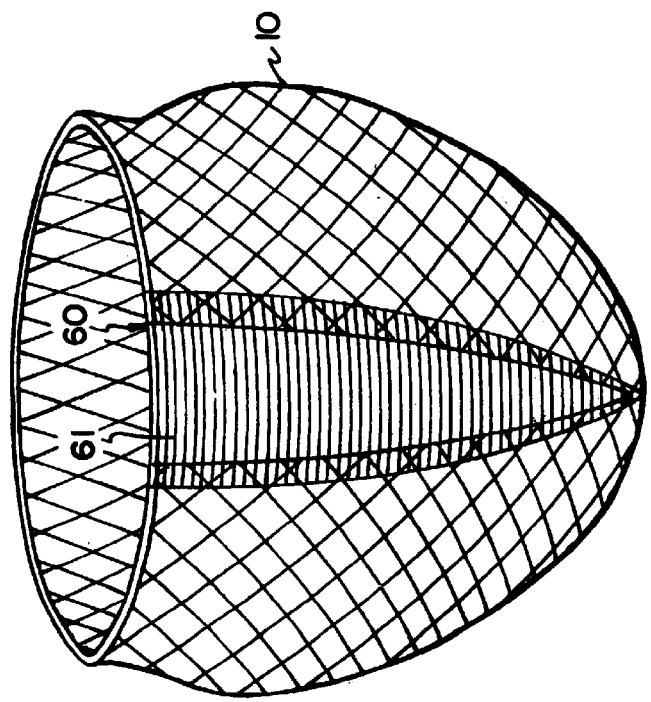
FIG. 10 is a perspective view of an alternate embodiment of a cardiac constraint device according to the present invention.

In another embodiment, the jacket 10 includes a band 60 (preferably a vertical band, i.e., oriented parallel to longitudinal axis AA–BB of the heart H when in use) of elastic material, such as SILASTIC® material (FIG. 10). The vertical band of elastic material 60 allows the jacket 10 to be stretched to encompass a diseased heart with an increased cardiac volume. When the elastic material is not stretched (i.e., relaxed), the jacket 10 defines a volume that approximates the maximum cardiac volume of a healthy heart. Thus, as the heart undergoes reverse remodeling, the elastic band 60 in the jacket 10 relaxes and the maximum volume defined by the jacket 10 is decreased.

Preferably, the vertical elastic band jacket 10 is constructed using a band of horizontally oriented (i.e., oriented circumferentially around the heart) elastic rods 61. Preferably the rods are generally cylindrical to reduce the effect of fibrosis upon contraction of the rods. Alternately, the vertical elastic band 60 may be a solid uniform sheet of elastic material, preferably an elastic material with a smooth, slippery surface is used (to reduce fibrotic adhesions).

I. Vertical Spring Tensioning Device

Figure 11:
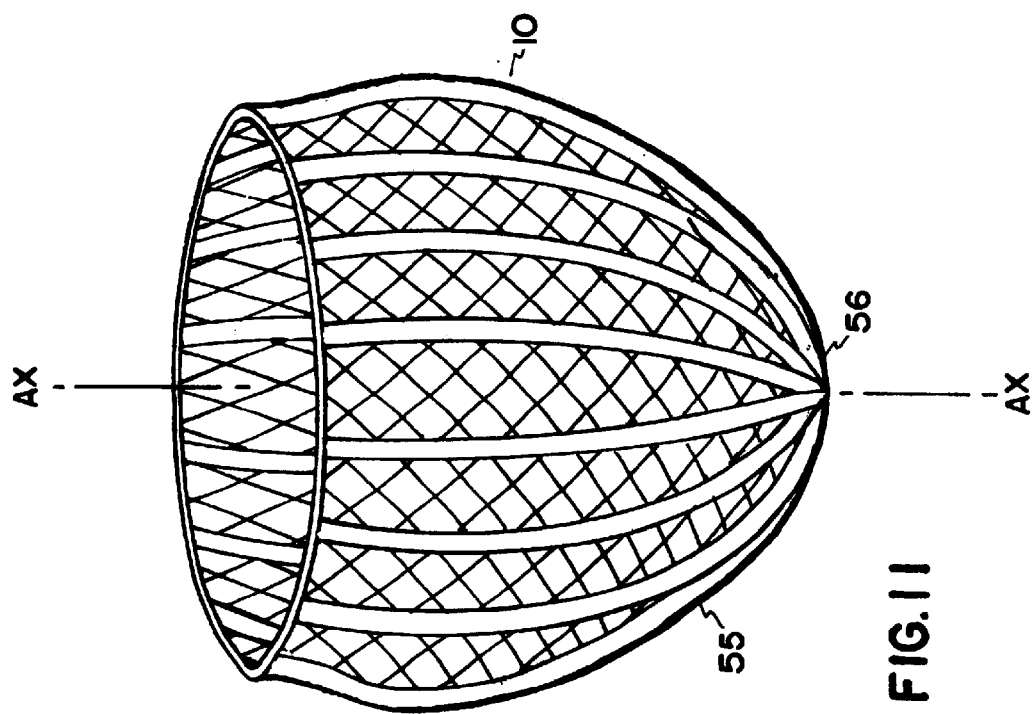
FIG. 11 is a perspective view of an alternate embodiment of a cardiac constraint device according to the present invention.
Figure 13:
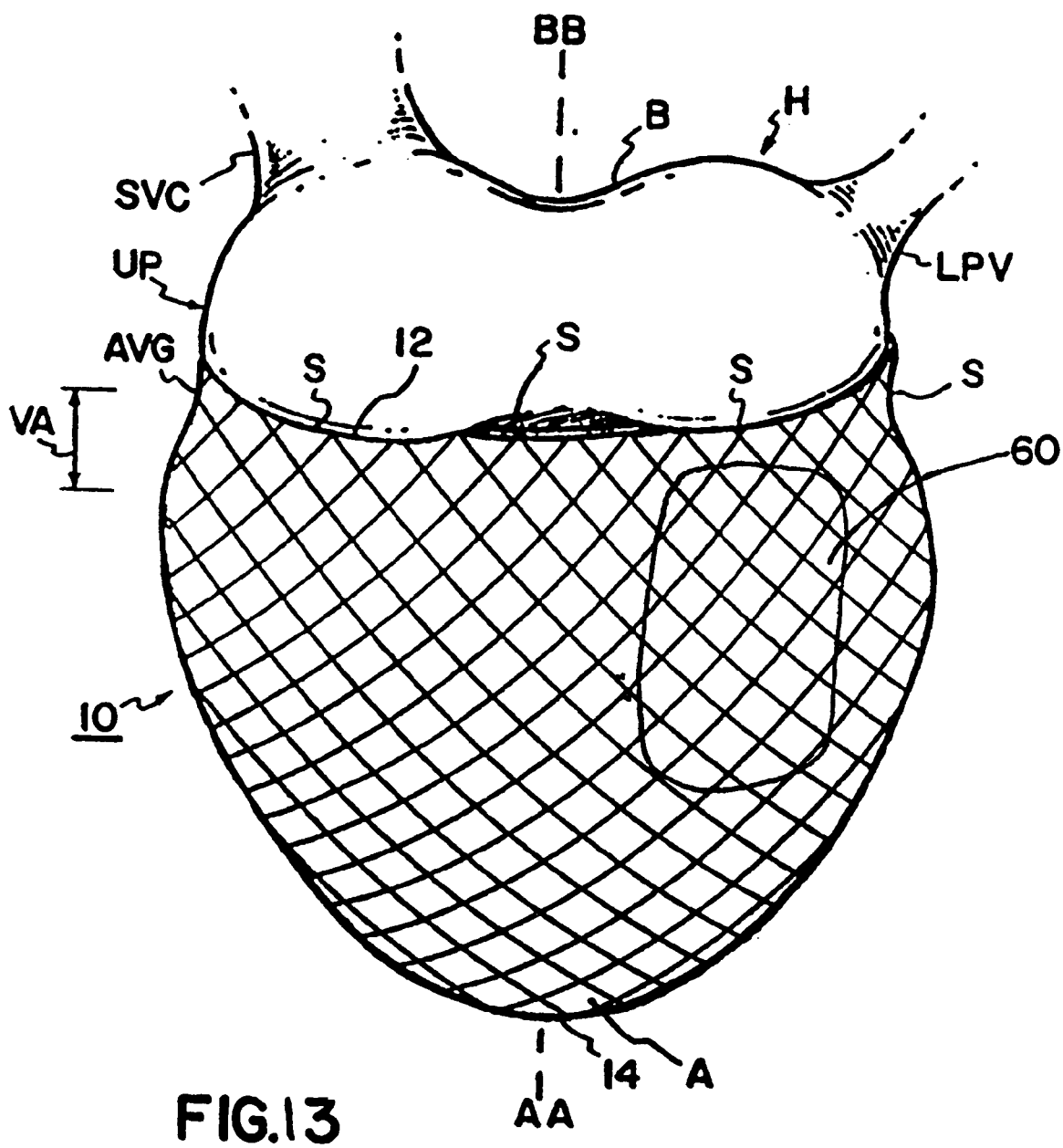
FIG. 13 is a side elevation view of a diseased heart with an embodiment of the device shown in place.

In an alternate embodiment, the jacket 10 includes a vertically oriented spring tensioning device 55 (See, e.g., FIG. 11). The vertically oriented spring tensioning device may be constructed, for example, from a plurality of radially positioned, spaced, ribs having a first end, configured to lie proximate the apex 56 of the heart when in use, and second end, configured to lie proximate the AV groove when in use. The ribs may be constructed from a material such as nitinol, or other metal, polymer or composite material. The ribs 55 may be fastened to the jacket 10 material by a variety of mechanisms, including sutures, loops of material, elongate tubes of material, or threaded between the fibers 20 or filaments 30 of the jacket 10 material. In one embodiment, the first ends of at least a few of the ribs 55 are connected at the apex 56 of the jacket 10, which functions as a leverage point.

Figure 12:
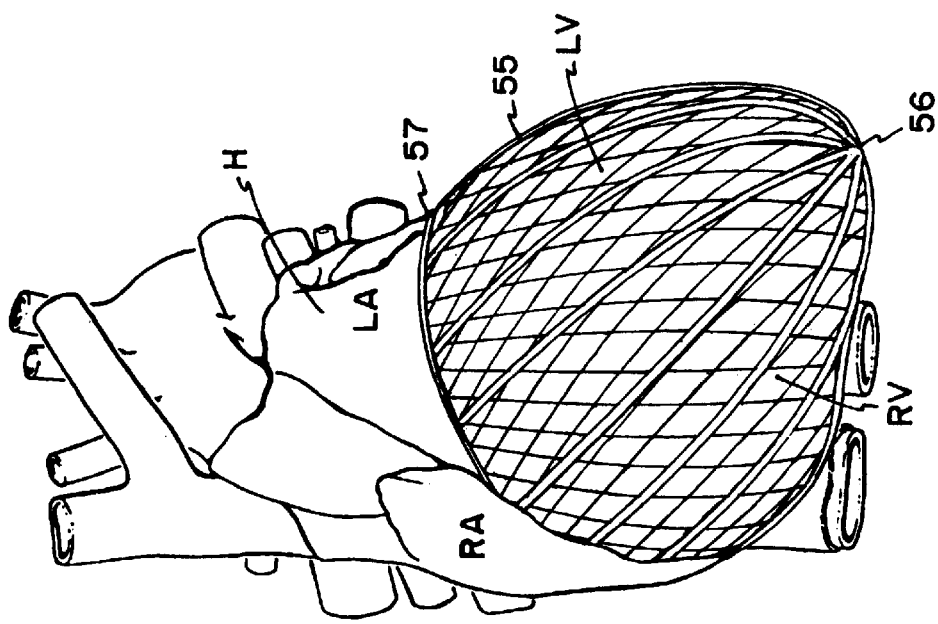
FIG. 12 side elevation view of a diseased heart with an embodiment of the device shown in place

In an alternate embodiment, the jacket 10 may further include a metal (or other material) ring 57 that fits over the enlarged ventricles and slides into place at the AV groove (See, e.g., FIG. 12). Preferably the ring 57 fits loosely around the AV groove and does not apply undue pressure. The ribs 55, described above, preferably extend from the ring 57 towards the apex 56 of the jacket 10. The second end of the ribs 55 may be fastened to the ring 57 by any suitable means, preferably by welding the ribs 55 to the ring 57. In this embodiment, other end of the ribs 55 (proximate the apex 56 of the jacket 10) preferably remain unfettered.

When in their initial, unloaded position (before installing on the heart H), volume of the jacket 10 defined by the ribs 55 approximates the size of a healthy heart (e.g., prior to enlargement due to disease). When installed onto the enlarged heart, the ribs 55 apply a gentle circumferential pressure (i.e., towards the axis AX—AX of the jacket 10) on the heart to halt and reverse cardiomegaly.

Generally, the ribs 55 are curved to follow the contours of the external surface of the heart H and to snugly fit the heart H at its enlarged diseased state. Preferably the ribs 55 are shaped such that, when fit over an enlarged diseased heart H, the ribs exert a compressive force. Preferably, the compressive force encourages reverse remodeling of the heart.

As the heart ventricle muscles under go reverse remodeling, the ribs 55 maintain pressure on the cardiac surface to encourage continued reverse remodeling, until the heart H size returns to a size that approximates the size of an undiseased (i.e., unexpanded) heart H. Once the heart obtains a size that approximates that of an undiseased heart, the ribs 55 relax and no longer compress the heart H. Advantageously, this embodiment provides a continuous compressive force on the heart H that is not hindered by fibrosis and/or adhesions.

J. Other

In some embodiments, it may be useful to include other elements to facilitate the size reduction process. For example, a biomaterial that is known to inhibit fibrous ingrowth or encapsulation may be incorporated into the jacket. Examples of such biomaterials include hyaluronic acid (active ingredient in Seprafilm, a commercially available film material from Genzyme Corporation), polyethylene glycol (active ingredient in FocalSeal-L, a commercial product from Focal, Inc.), and polyvinylpyrolidone.

In one embodiment, the biomaterial lines all or part of interior and/or exterior surface of the jacket 10. Preferably, the biomaterial is positioned between the jacket 10 and the epicardial surface to prevent fibroblasts from the cardiac tissue infiltrating the jacket 10, thereby inhibiting fibrous ingrowth and encapsulation of the jacket 10. The biomaterial can be positioned uniformly along the inner surface of the jacket 10, or only in specified locations along the inner surface of the jacket 10. For example, the biomaterial may only be located between the jacket 10 and an underlying epicardial coronary artery, to facilitate identification of, and access to these arteries.

Inclusion of a biomaterial in the device is particularly advantageous during subsequent operations on the heart, for example coronary artery bypass surgery.

From the foregoing, a low cost, reduced risk method and device are taught to treat cardiac disease. The invention is adapted for use with both early and later stage congestive heart disease patients. The invention reduces the enlargement rate of the heart as well as reducing cardiac valve regurgitation.

What is claimed is:

1. A cardiac constraint device for treating disease of a heart comprising:
    a jacket of flexible material defining an internal volume between an open upper end and a lower end; said jacket adapted to be secured to the heart to snugly conform to an external geometry of the heart and to constrain circumferential expansion of the heart beyond a maximum adjusted volume during diastole and permit substantially unimpeded contraction of the heart during systole; and
    an adjustment mechanism comprising a piezoelectric material, wherein said piezoelectric material is capable of reducing said internal volume defined by said jacket after said jacket is secured to the heart.

2. A device according to claim 1 wherein said piezoelectric material comprises polyvinylidine fluoride.

3. A cardiac constraint device for treating disease of a heart comprising:
    a jacket of flexible material defining an internal volume between an open upper end and a lower end; said jacket adapted to be secured to the heart to snugly conform to an external geometry of the heart and to constrain circumferential expansion of the heart beyond a maximum adjusted volume during diastole and permit substantially unimpeded contraction of the heart during systole; and
    an adjustment mechanism comprising:
        at least one stay element positioned circumferentially around said jacket, wherein said at least one stay element is configured to cinch said jacket material to effectively decrease said internal volume defined by said jacket after said jacket is secured to the heart; and
        at least one receptacle configured to receive said at least one stay element and position said at least one stay element on an external surface of said jacket.

4. A device according to claim 3 comprising a plurality of stay elements.

5. A device according to claim 3 wherein said jacket material comprises a biodegradable material and said stay element and receptacle comprise non-biodegradable material.

* * * * *